US007944208B2

(12) United States Patent
Dutto et al.

(10) Patent No.: US 7,944,208 B2
(45) Date of Patent: May 17, 2011

(54) ACTIVE IMAGE AREA POSITIONING WITH ADJUSTABLE PATIENT BENCH PERMITTING CHAIR-SHAPED PATIENT TRANSPORT INTO AND OUT OF AN OPEN MRI APPARATUS SYSTEM

(75) Inventors: Roberto Dutto, Genoa (IT); Marco Monaldi, Genoa (IT)

(73) Assignee: Paramed Medical Systems, Inc., North Andover, MA (US)

( * ) Notice: Subject to any disclaimer, the term of this patent is extended or adjusted under 35 U.S.C. 154(b) by 192 days.

(21) Appl. No.: 12/276,762

(22) Filed: Nov. 24, 2008

(65) Prior Publication Data
US 2009/0289633 A1  Nov. 26, 2009

(30) Foreign Application Priority Data

Nov. 23, 2007 (IT) .............................. TO2007A0840

(51) Int. Cl.
*G01V 3/00* (2006.01)
*A61B 5/05* (2006.01)
(52) U.S. Cl. ........ 324/309; 324/321; 324/307; 324/318; 324/319; 600/415; 600/410; 600/411; 600/421
(58) Field of Classification Search .......... 324/300–322; 600/407–435; 382/128–131
See application file for complete search history.

(56) References Cited

U.S. PATENT DOCUMENTS

| 4,985,678 | A | 1/1991 | Gangarosa et al. | |
| 5,008,624 | A | 4/1991 | Yoshida | |
| 5,153,546 | A | 10/1992 | Laskaris | |
| 5,592,090 | A | 1/1997 | Pissanetzky | |
| 5,724,970 | A * | 3/1998 | Votruba et al. ................ | 600/415 |
| 5,772,595 | A * | 6/1998 | Votruba et al. ................ | 600/415 |
| 5,810,006 | A * | 9/1998 | Votruba et al. ................ | 600/415 |
| 5,874,880 | A | 2/1999 | Laskaris et al. | |
| 5,899,859 | A * | 5/1999 | Votruba et al. ................ | 600/415 |
| 6,023,165 | A | 2/2000 | Damadian et al. | |
| 6,075,364 | A | 6/2000 | Damadian et al. | |
| 6,246,239 | B1 * | 6/2001 | Krogmann et al. ........... | 324/318 |
| 6,404,202 | B1 | 6/2002 | Damadian et al. | |
| 6,411,187 | B1 | 6/2002 | Rotem et al. | |
| 6,416,219 | B1 * | 7/2002 | Pflaum et al. ................ | 378/209 |
| 6,456,075 | B1 | 9/2002 | Damadian et al. | |

(Continued)

FOREIGN PATENT DOCUMENTS

EP       1519390 A2      3/2005

(Continued)

*Primary Examiner* — Melissa J Koval
*Assistant Examiner* — Tiffany A Fetzner
(74) *Attorney, Agent, or Firm* — Venable LLP; Robert S. Babayi; Leigh D. Thelen (57) ABSTRACT

A Magnetic Resonance Imaging System consisting of a magnet (10) with a U-shaped frame (15), whose pole faces define an open magnetic imaging area [R] for a patient, and a magnetic field generator (17) that is controlled to generate magnetic fields inside the magnetic imaging area; a transport system (30) associated with the magnet has a support structure (20) that defines a movement path through the magnetic imaging area. The transport system (30) also includes a bench (40) to support the patient. The transport system (30) can slide the bench (40) along the support structure so that the patient can be introduced into and extracted from the magnetic imaging area. The bench (40) may further include a non-reclinable support part (41) coupled to reclinable support parts (42 and 43) at opposing ends to allow the position of patient to be rotatably changed on the bench (40).

15 Claims, 9 Drawing Sheets

U.S. PATENT DOCUMENTS

| | | |
|---|---|---|
| 6,462,548 B1 | 10/2002 | Havens |
| 6,677,753 B1 | 1/2004 | Danby et al. |
| 6,794,871 B2 * | 9/2004 | Imai et al. ................ 324/318 |
| 6,822,447 B1 * | 11/2004 | Yamagata ................ 324/318 |
| 6,822,449 B1 | 11/2004 | Bonanni et al. |
| 6,828,792 B1 | 12/2004 | Danby et al. |
| 7,057,389 B2 * | 6/2006 | Kamimura et al. ........ 324/318 |
| 7,102,353 B1 | 9/2006 | Damadian |
| 7,239,906 B1 * | 7/2007 | Green et al. ............ 600/407 |
| 7,663,366 B2 * | 2/2010 | Takamori ................ 324/318 |
| 7,697,971 B1 * | 4/2010 | Green et al. ............ 600/415 |
| 2003/0207765 A1 | 11/2003 | Bower et al. |
| 2006/0197530 A1 | 9/2006 | Damadian et al. |
| 2006/0260050 A1 * | 11/2006 | Manzione ................ 5/601 |
| 2009/0189608 A1 * | 7/2009 | Liu et al. ................ 324/321 |
| 2009/0289633 A1 * | 11/2009 | Dutto et al. ............. 324/321 |
| 2010/0102814 A1 * | 4/2010 | Satragno et al. ......... 324/309 |

FOREIGN PATENT DOCUMENTS

| | | |
|---|---|---|
| EP | 1526586 A2 | 4/2005 |
| JP | 10127595 A | 5/1998 |
| JP | 10234701 A | 9/1998 |
| JP | 2002334620 A | 11/2002 |
| JP | 2002352648 A | 12/2002 |
| JP | 2005063768 A | 3/2005 |
| WO | WO-03035575 A1 | 5/2003 |
| WO | WO-2006035065 A2 | 4/2006 |

* cited by examiner

ACTIVE IMAGE AREA POSITIONING WITH ADJUSTABLE PATIENT BENCH PERMITTING CHAIR-SHAPED PATIENT TRANSPORT INTO AND OUT OF AN OPEN MRI APPARATUS SYSTEM

CROSS-REFERENCE TO RELATED APPLICATIONS

This application claims priority to Italian patent application TO2007A000840 filed Nov. 23, 2007, the subject matter of which is incorporated herein by reference.

FIELD OF THE INVENTION

The present invention generally relates to a positioning system that orients a patient for examination in a medical equipment and more particularly to positioning a patient in an Magnetic Resonance Imaging System (MRI system).

BACKGROUND OF THE INVENTION

Open MRI system are known. One such MRI system is disclosed in the U.S. Pat. No. 6,023,165. This prior art MRI has a magnet with opposing poles that create an open MRI imaging area comprising a patient-receiving gap. In one embodiment, a room formed by walls and ceiling and front wall encloses the patient-receiving gap which is between the magnet poles. The legs of a magnet yoke extend through the wall so that the electromagnet is outside of the room housing the gap.

According to another disclosed embodiment in this prior art, the magnet has a C-shaped yoke with the opposing poles creating the patient-receiving gap. A body rest is positioned within the gap and is mounted to pivot between a vertical orientation and a horizontal orientation. A pair of upstanding vertical supports are positioned with the body rest between them. The body rest is mounted on the supports by a pair of pivots. The body rest may also possess a seat to sit a vertically oriented patient.

This prior art also discloses a horizontal platform at the lower end of the body rest that allows a patient to stand on the platform and to lean against the body rest to facilitate patient immobilization within the gap. This arrangement allows for MRI studies of the upright patient where the studies can be performed while the human body, spine, joints, central nervous system and other organs are acted upon by the gravitational field, loading it as it normally loads the upright human body. According to still another embodiment in this prior art, the body rest is situated within a frame and is mounted to pivot about its longitudinal axis. This structure allows the patient to be tilted within the patient-receiving gap. Also disclosed in this prior art is a method of performing magnetic resonance where a patient is positioned in a prone position for receiving magnetic resonance signals while within the patient-receiving gap. The patient's anterior-posterior axis is at an arbitrary angle with respect to the magnetic field that is not zero and not orthogonal.

Another known open MRI system is disclosed in the U.S. Pat. No. 6,404,202. This prior art system has a C-shaped MRI magnet coupled to a pair of opposed ferromagnetic poles that face each other and define a patient-receiving gap. The magnet is positioned on a surface via two support columns. A mobile patient-positioning device has a patient support for positioning the patient for MRI scanning. The patient support is rotatable through a range of orientations. The patient support can be positioned horizontally or in a slanted position. The patient disposed on the mobile patient-positioning can then be moved horizontally into and out of a patient-receiving space in the MRI magnet at a predetermined angle or orientation. Another embodiment of this prior art includes a plurality of patient-positioning devices in which a series of patients can be placed in a ready state while one patient is within the patient-receiving space.

However, there exists a need to improve the known open MRI systems to allow for more flexibility in positioning of patients for examination.

SUMMARY OF THE INVENTION

Briefly, according to the present invention, a magnetic resonant imaging system comprises a magnet having opposing poles that define an open magnetic resonance imaging area for receiving magnetic fields generated by the magnet. In one exemplary embodiment, the magnet has a substantially U-shaped yoke. A transport system comprising a support structure having a track in a fixed position relative to the magnet supports a bench for positioning a patient within the resonance imaging area. A drive unit, e.g., a motor, moves the bench along a movement path, e.g., a longitudinal path, on the track into and out of the open magnetic resonance imaging area. The bench has at least one rotation point where at least one part of the bench is rotatable around a rotational axis for positioning the patient in a desired rotated or slanted position within the open magnetic resonance imaging area. In another exemplary embodiment, the transport system is movable along a vertical axis for elevating and lowering the bench.

According to some of the more detailed features of the present invention, the bench comprises a non-reclinable support part and at least one reclinable support part that is rotatably coupled to the non-reclinable support part at a rotation point. In one exemplary embodiment, two reclinable support parts are rotatably coupled to opposing end of the non-reclinable support part at corresponding rotation points.

According to other more detailed features of the present invention, the track of the transport system comprises a transmission belt loop made of non-metallic material that is driven by the driver unit for moving the bench along the movement path. In one exemplary embodiment, the driver unit drives at least one pulley that is engaged with the transmission belt loop at a drive point.

According to still other more detailed features of the present invention, the transport system comprises a pantograph mechanism such that a rotational movement at one part of the bench corresponds to a rotational movement at another part of the bench. According to one exemplary embodiment, the pantograph mechanism comprises telescopic supports coupled to the one part and to the other part of the bench. In another exemplary embodiment, the bench is rotated to a desired position automatically in response to a control signal generated by a system operator. The bench may also comprise movable parts for adjusting the position of the bench such that the movable parts are made of non-ferromagnetic material.

DETAILED DESCRIPTION OF THE INVENTION

The invention allows moving or otherwise suitably positioning a patient for examination in an MRI system. The system comprises:

(1) a magnet comprising a magnetic field generator;

(2) a transport system having a support structure having a track fixedly positioned relative to the magnet;

(3) a bench, e.g., carriage, seat, chair or table, positioned on the support structure; and (4) a drive unit, e.g., a motor, that moves the bench along a movement path.

In one embodiment, the transport system includes a vail or track defining the movement path to accommodate the positioning of the patient within by the MRI system. In one exemplary embodiment, the bench moves along the track so that the patient can be easily introduced into and extracted from the open magnetic imaging area.

Preferably, the systems of the present invention is used for open magnetic resonance imaging, also know as open MRI, in which the space above the magnetic area where the patient is examined is open and free from obstruction. In this way, the open MRI structure prevents claustrophobia and other adverse sensations normally associated with closed MRI structures.

While one aspect of the present invention relates to a positioning system for the examination of patients in an open MRI systems, other aspects of the present invention can also be configured in such a manner as to allow patient positioning in various types of medical equipment for examination.

A positioning system for MRI examination includes a moveable transport system that is displaced along a track that defines a movement. In one exemplary embodiment, a bench having a non-reclinable part, for example one in a fixed horizontal position, with one or more associated reclinable parts, for example, two parts at opposing ends of the non-reclinable part, allows the position of the patient to be changed around one or more rotational axis, for example, in a slanted position.

With reference to the drawings, the MRI system of the present invention comprises a magnet (10). The magnet (10) includes a U-shaped frame (15) made of ferromagnetic material that couples a pair of poles having opposing faces (11) (only one of these can be seen in FIG. 1) that are positioned substantially in parallel along a substantially horizontal axis.

In one embodiment, the magnet (10) is placed in a vertical position so that the horizontal axis X is arranged above a central part (15a) of the yoke of the magnet (10). The pole faces (11) define an open magnetic imaging area [R] for receiving magnetic fields (10) generated by the magnet (10) where a patient can be positioned for MRI study. The magnet (10) also includes magnetic field generator devices (17), that can be operated to generate the magnetic fields in the open magnetic imaging area [R]. The magnetic field generators (17) are arranged around each one of the pole faces (11).

The MRI system is also fitted with an automated transport system (30). The transport system (30) include a support structure (20) which is at a fixed position relative to the magnet (10). The support structure (20) comprises a track that is arranged in such a manner as to extend through the open magnetic imaging area [R] along a defined movement path. The movement path traverses through the open magnetic imaging area [R].

The transport system (30) also includes a trolley (31) which can slide along movement path defined by the track of the support structure (20) to move a patient positioned on a bench 40 into and out of the magnetic imaging area [R]. Preferably, the transport system (30) is realised in such a way so as to prevent exposing ferromagnetic materials to the magnetic imaging area [R]. In one embodiment, the conductive parts of the transport system (30) are contained within a non-ferromagnetic enclosed box or housing. This arrangement prevents the perturbation of the magnetic field that the ferromagnetic bodies produce when placed inside the electromagnetic field, thereby avoiding non-homogeneity of the electromagnetic field produced by the ferromagnetic bodies that would strongly deteriorate the quality of the imaging. In designing the transport system of the invention, consideration is given to the fact that the magnetic resonance signal, which generates the image, is an electromagnetic wave at the resonant frequency of the magnet which can vary from a few MHz to several hundreds of MHz. The presence of electrically conductive materials disturbs the propagation of electromagnetic waves and can, therefore, deteriorate the quality of the image.

Figure 1:
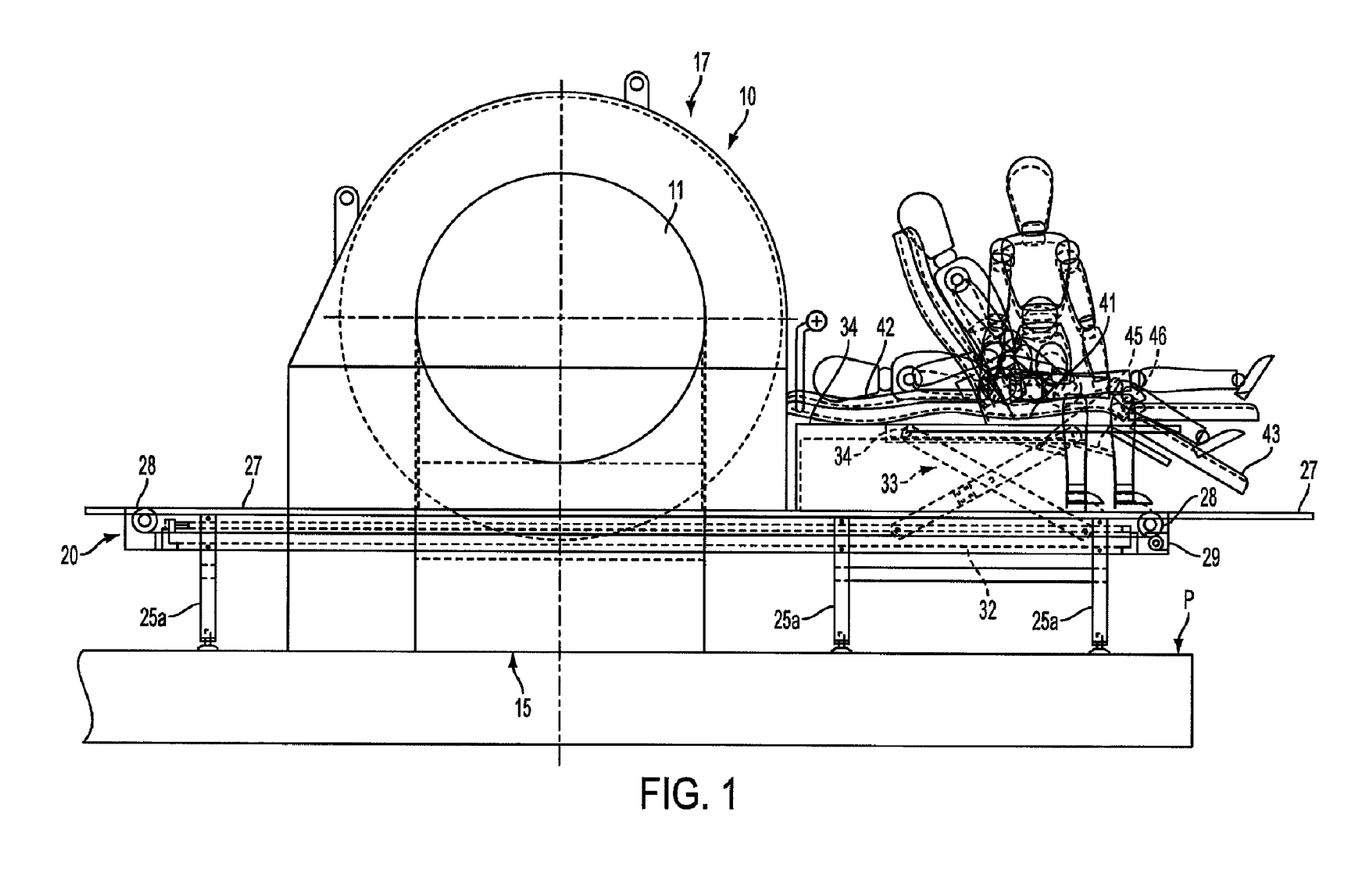
FIG. 1 is a side view of a MRI system depicting the positioning of a patient in accordance with one exemplary embodiment of the invention.
Figure 2:
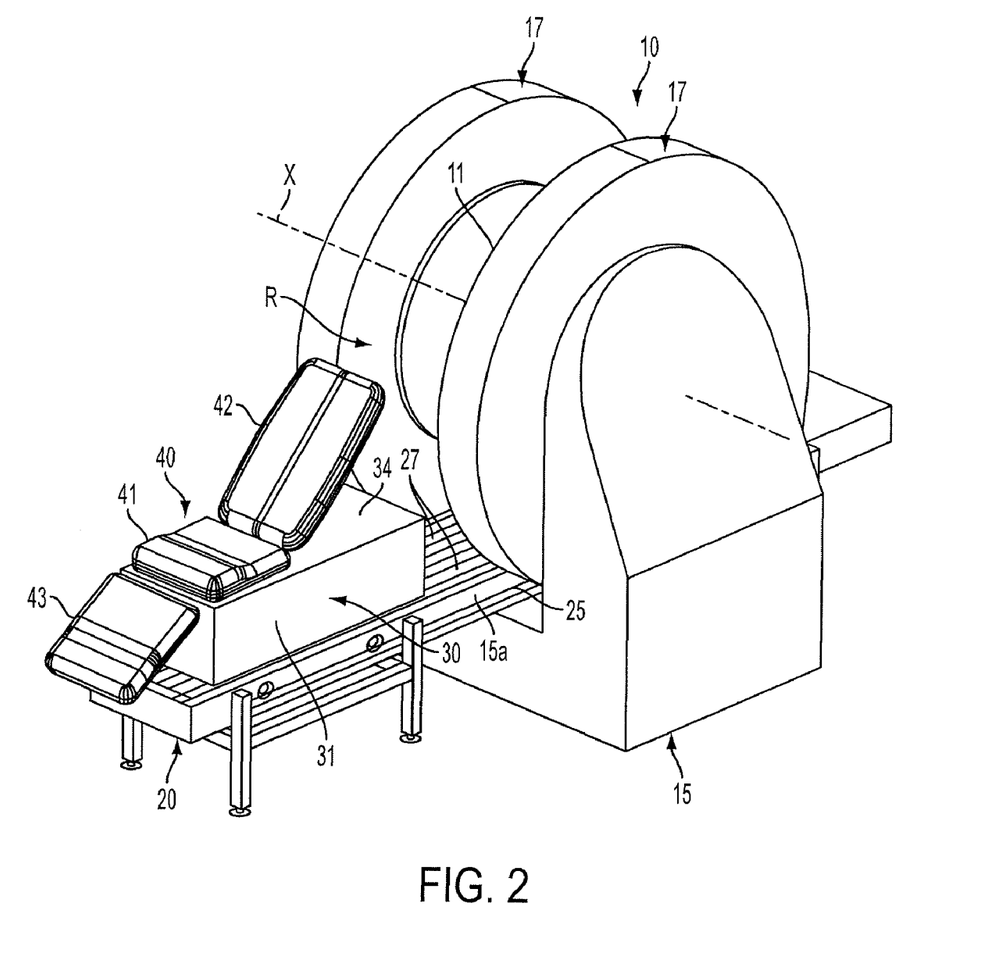
FIG. 2 is an isometric view of the MRI system of FIG. 1.
Figure 3:
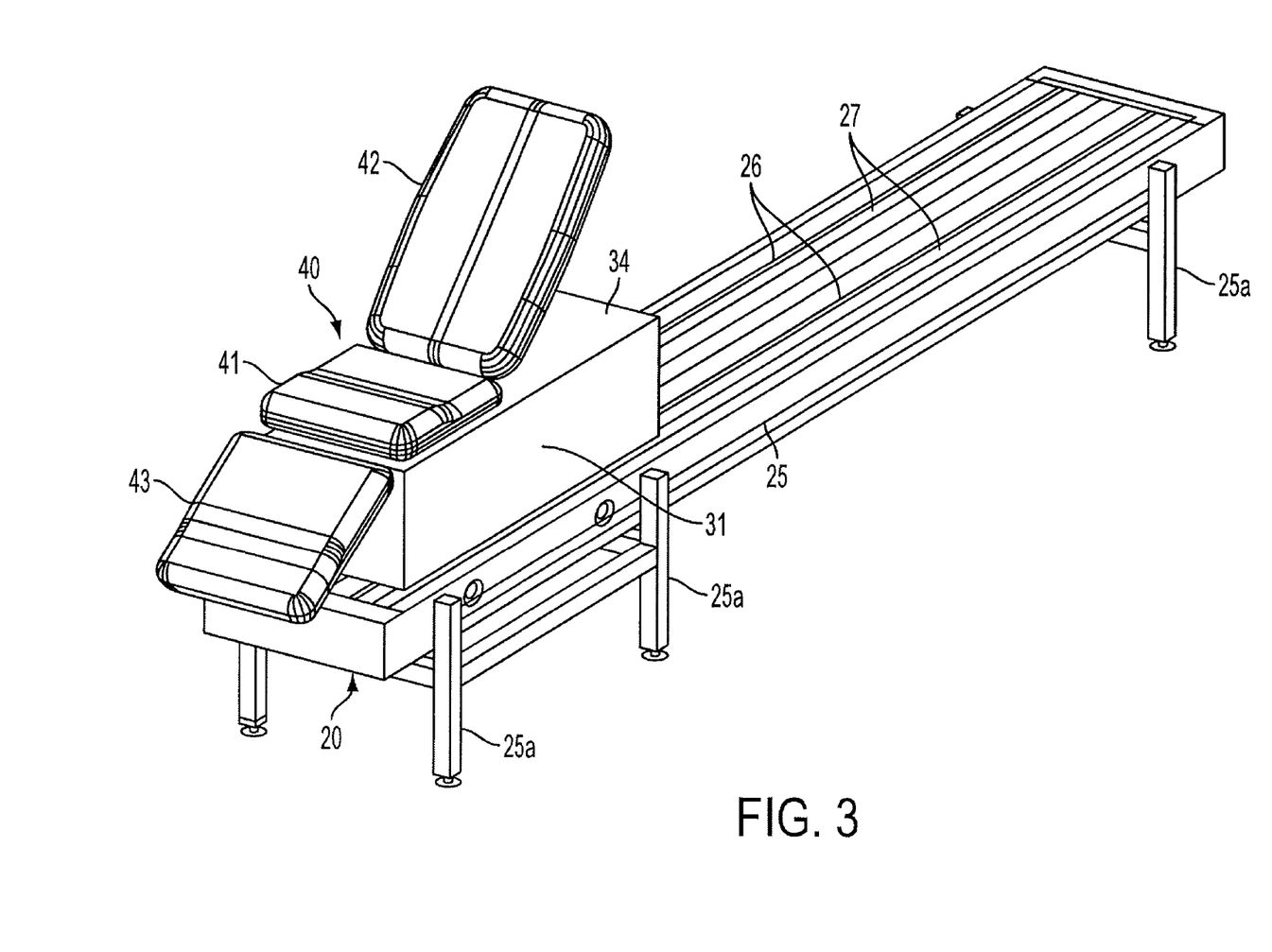
FIG. 3 is an isometric view of one exemplary transport system used in the MRI system of FIG. 1.
Figure 5:
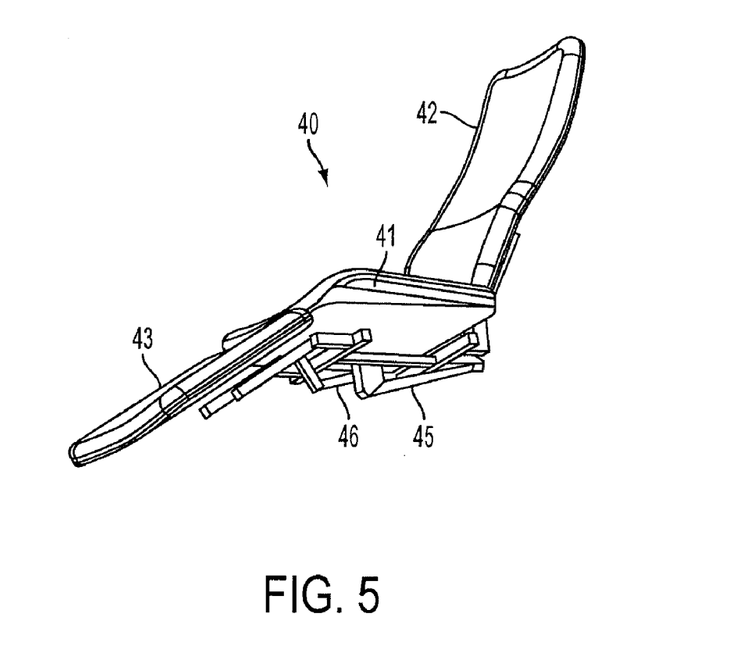
FIG. 5 is an isometric view of FIG. 4.

In order to overcome the difficulties mentioned above, those parts of the transport system (30) in proximity with the open magnetic area [R] are made from plastic materials with the addition of small metallic non-ferromagnetic components. An exemplary arrangement for the transport system (30), as illustrated in FIGS. 1 and 5, envisages that the support structure (20) is fitted with a box-type longitudinal element (25), fitted to the magnet (10) and resting on the floor [P] of the equipment room by means of adjustable support legs (25a). Along the box-type longitudinal element (25), a pair of channels have been machined (26) forming a track. Inside the longitudinal element (25) there is a pair of parallel transmission belts (27), made from non-metallic material, wound around in a loop with the respective terminal belt pulleys (28) arranged at the extremities of the box-type longitudinal element (25), positioned outside of the magnetic area [R]. At the extremity of the box-type longitudinal element there is a drive unit, such as an electrical motor (29), that engages the belts (27) at corresponding drive points. In one exemplary embodiment, the trolley (31) includes a base element (32) fixed to the upper part of the drive belts (27) and arranged inside the box-type element (25). The base element (32) is connected to a pantograph mechanism (33), whose arms pass through the channels (26) of the box-type element (25). An upper element (34) of the trolley (31) is mounted on the pantograph element (33), which can be lifted with respect to the base element (32) by the pantograph mechanism (33).

On the trolley (31) upper element (34), there is the moveable bench (40) that supports the patient. In one exemplary embodiment, the bench (40) extends along the direction of travel of the trolley (31). In accordance with one embodiment of the invention, the bench (40) comprises a non-reclinable support part (41), e.g., a fixed central part having a substantially horizontal position, with the respective reclinable support parts (42 and 43) rotatably coupled to the opposite extremities of the non-reclinable support part (41), to allow rotatably changing the position of the patient on the bench, for example, to position the patient in a slanted position.

Figure 4:
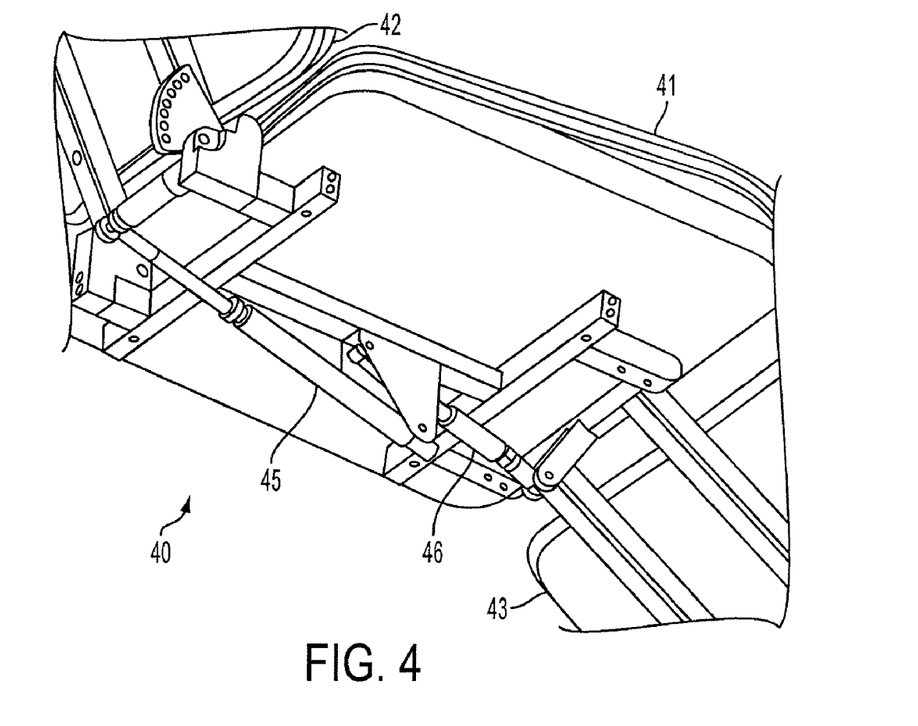
FIG. 4 is a bottom view of an exemplary pantographic mechanism for the transport system of FIG. 3.

Adjustment of the reclinable parts (42 and 43), which constitute the advantage of providing a backrest and footrest respectively for the bench (40), is done in an automated manner by means of hydraulic cylinders (45 and 46) made from non-ferromagnetic materials. In FIGS. 4 and 5, the bench (40) is illustrated in a large scale so as to highlight the parts relevant to movement of the backrest (42) and footrest (43). For each of the hydraulic cylinders (45 and 46) one extremity is hinged to the central part of the support (41), while the other extremity is hinged to the backrest (42) and footrest (43) respectively. Naturally the hydraulic cylinders (45 and 46) are connected to a conventional type of hydraulic plant (not illustrated) mainly consisting of an electrical pump, small tank, servo-valves for adjustment and control purposes, control panel and all the components normally required for the realisation of an hydraulic control plant. The hydraulic cylinders (45 and 46) move the parts (42 and 43) of the bench (40) in an independent and gradual manner to obtain the correct position to be acquired. In one exemplary embodiment, movement of the hydraulic cylinders (45 and 46) is controlled by means an operator using a control panel in response to a control signal (not illustrated), for example, by means of activating push-buttons and switches.

Figure 6:
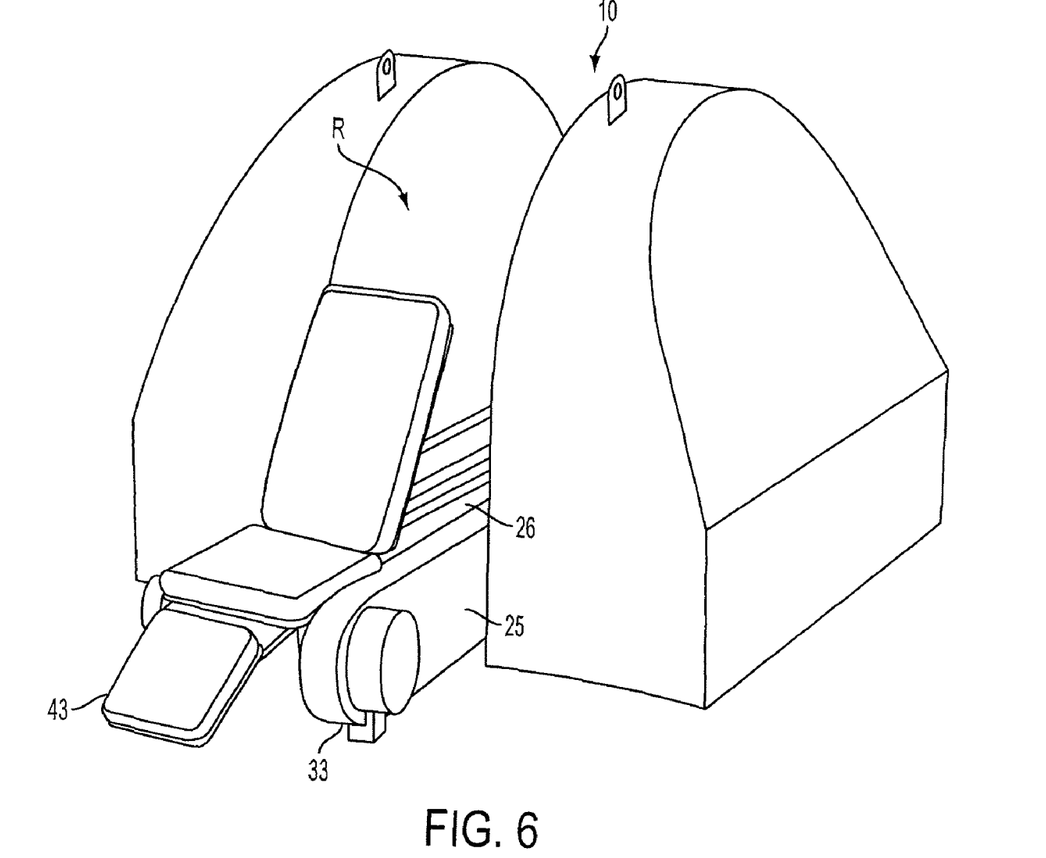
FIG. 6 is an isometric view of an MRI system according to another exemplary embodiment of the present invention.

FIG. 6 illustrates another type of arrangement in which the elements corresponding to those in the first arrangement have been assigned with the same reference numbers. This alternative arrangement envisages that the support structure (20) includes a pair of parallel box-type longitudinal elements (25'), along each of which there is a machined track channel (26). Inside each of the longitudinal elements (25') there is a transmission belt (not illustrated), made from a non-metallic material, that is wound in a loop around the respective terminal pulleys at corresponding drive points (not illustrated) arranged at the extremity of each of the box-type longitudinal elements (25), positioned outside the magnetic area [R]. At the extremity of each of the box-type longitudinal elements there is an electrical motor (not illustrated) that engages the belts at corresponding drive points.

In one embodiment, the trolley (31) is fixed to the upper part of the belts, and the bench (40) is then fixed to the trolley (31). According to this type of arrangement, and to guarantee the vertical movement of the bench (40), the box-type longitudinal elements (25') are supported, each one, by two telescopic support frames (33') situated at the extremities. The contemporary lifting and lowering of the telescopic support frames (33') generates the adjustment for the vertical position of the bench (40) irrespective of its horizontal position along the sliding structure.

Figure 7:
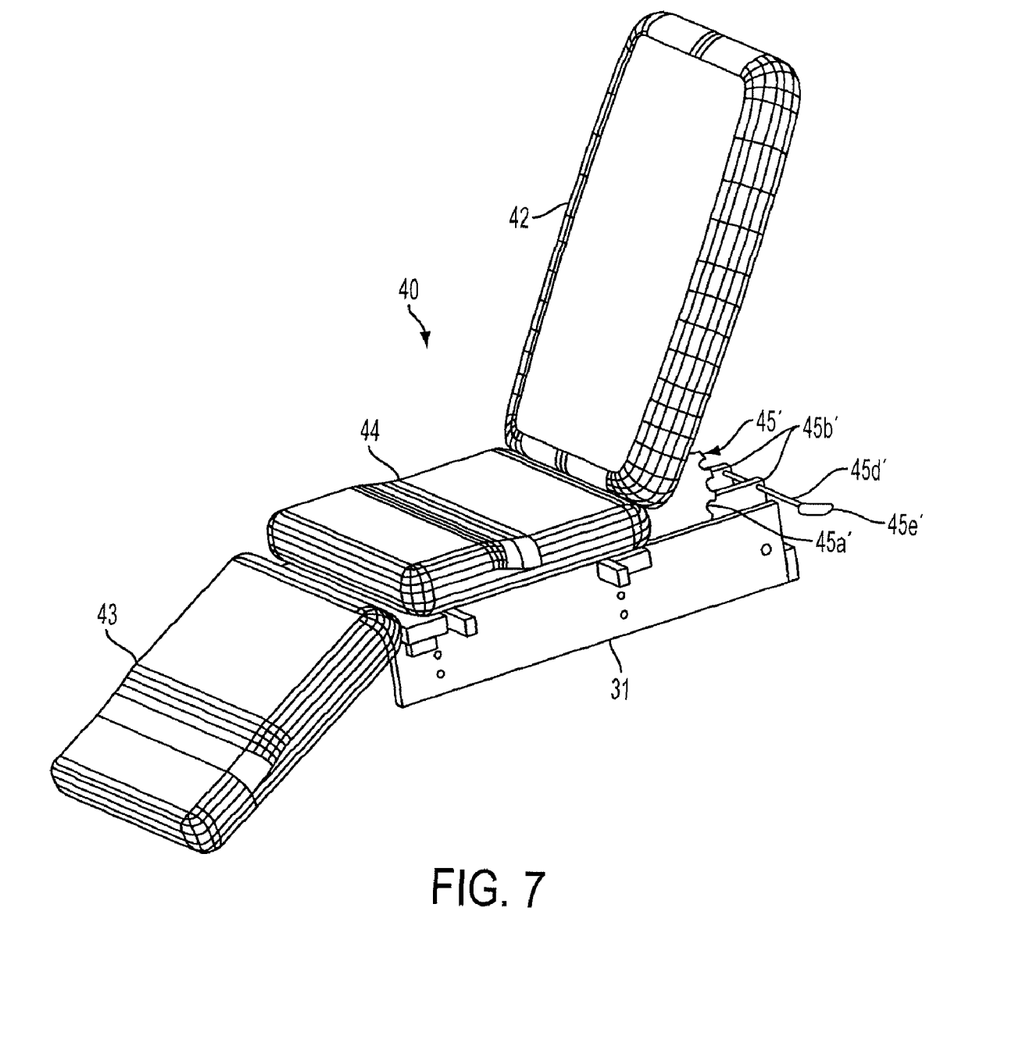
FIG. 7 is an isometric view of another exemplary transport system.
Figure 8:
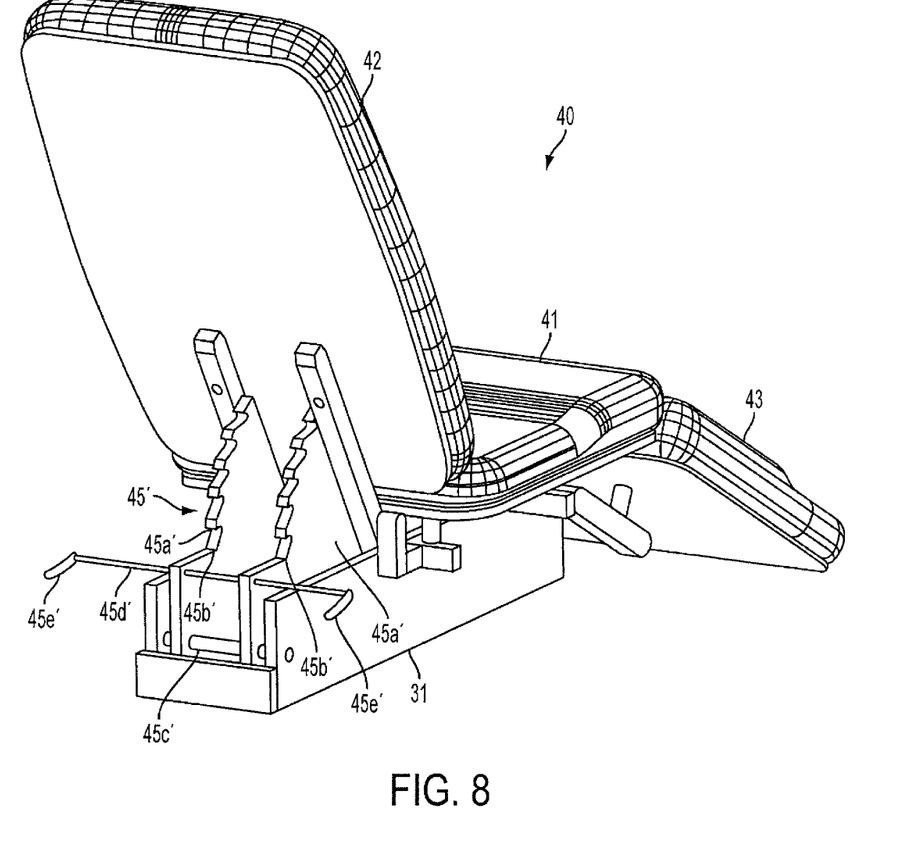
FIG. 8 is a rear view of the transport system of FIG. 8.

FIGS. 7 and 8 illustrate an alternative arrangement of the bench (40) for the equipment in FIG. 6. For this alternative arrangement the adjustment of the reclinable parts (42 and 43) is manual and done by means of the ratchet (45'), where in FIGS. 7 and 8, only the ratchet (45') associated with the backrest (42) can be seen.

This ratchet mechanism (45') also includes two sectors of a parallel toothed wheel (45a') fixed to the backrest (42) (the same is also true for the footrest (43)), on to each of which the respective pawls are geared (45b'). The pawls (45b') are fixed to a shaft (45') mounted on the frame of the trolley (31), for which they are able to rotate. In addition, a control shaft (45d') is fixed to the pawls. The manual positioning of the backrest is done by holding the backrest with one hand and by operating the pawls (45b') with the other hand by use of the appropriate lever (45e'), that is positioned at the extremity of the shaft (45d'), so as to be able to turn these towards the outside and to free them from the throat of the toothed wheel, (45a') on to which the pawls are engaged. The physical arrangement of the pawls (45b') is determined in such a way that, once the control shaft (45d') has been left free, the barycentre of the same causes the pawls to fall behind due to gravity and for them to be engaged into the throats of the toothed wheel (45a') relative to the new angular position of the backrest (42). The system is similar for smaller loads but is reduced in size.

Figure 9A:
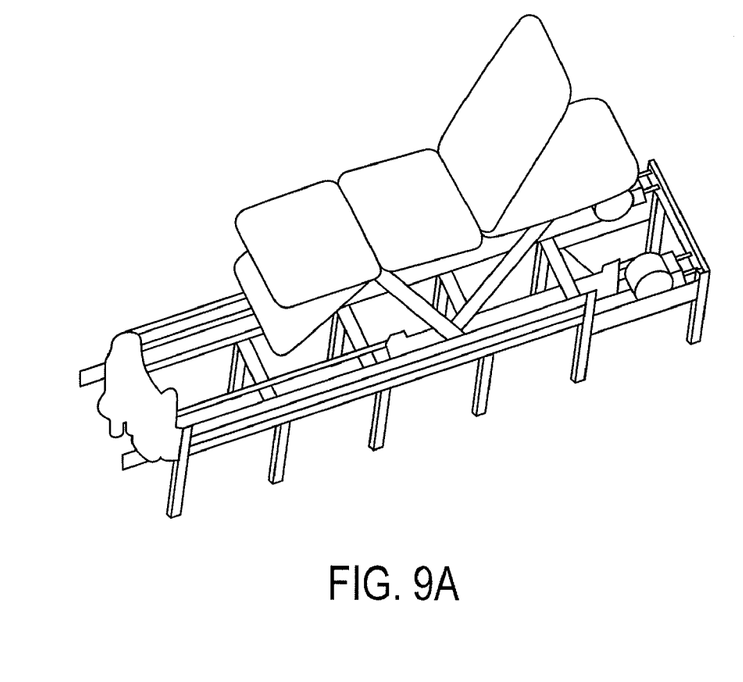
FIGS. 9(a) and 9(b) are isometric views of another embodiment of a positioning system for moving a patient along a movement path as well as in rotated and elevated positions.
Figure 9B:
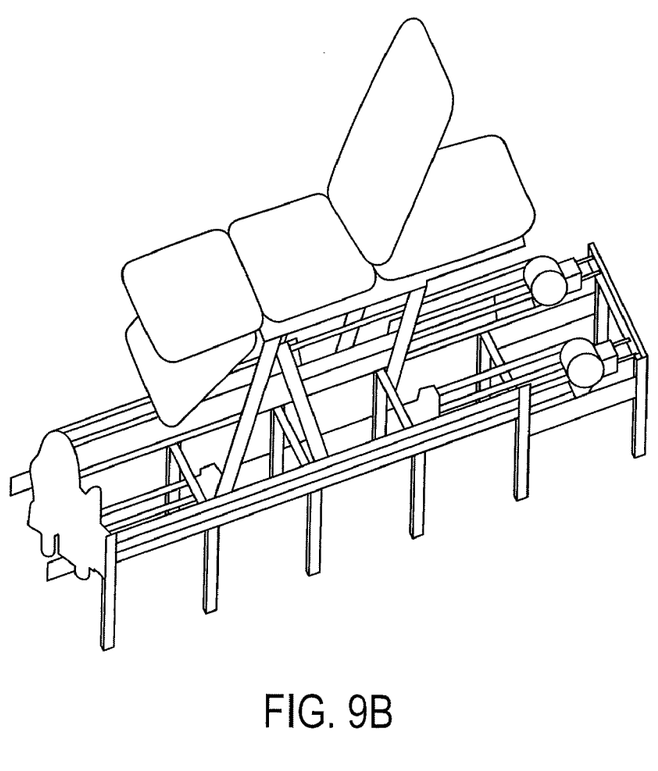
Figure 10A:
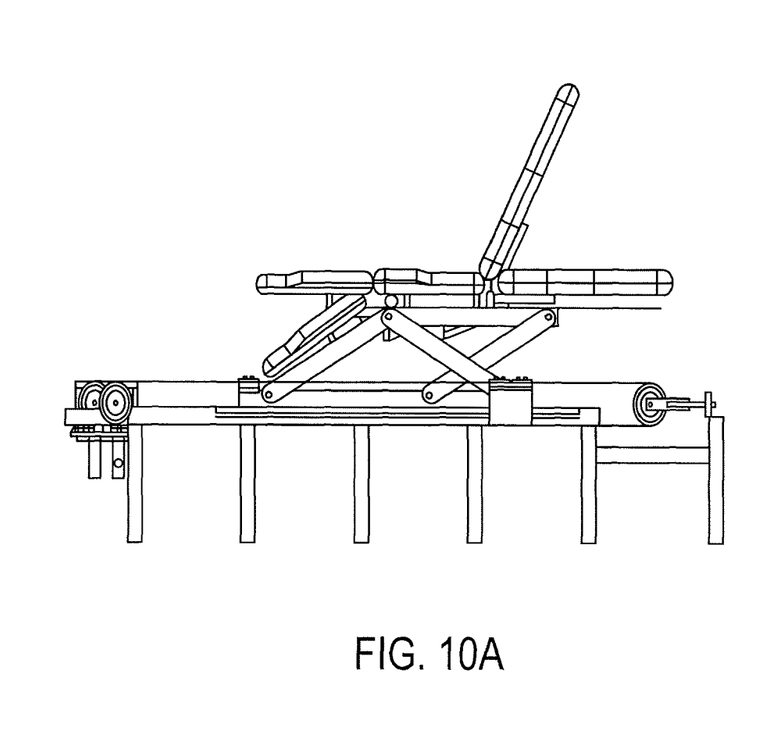
FIGS. 10(a) and 10(b) are side views of the embodiment of FIGS. 10(a) and 10(b) for positioning a patient along a vertical axis.
Figure 10B:
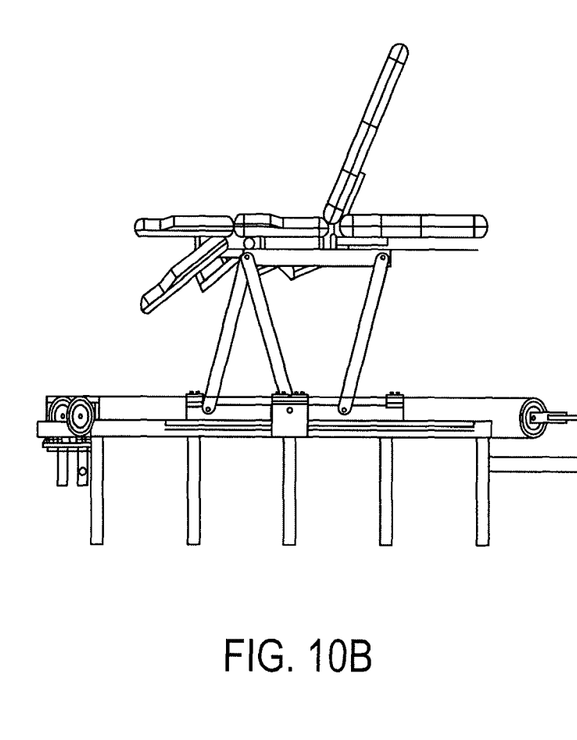

FIGS. 9(*a*) and 9(*b*) show another embodiment of a positioning system for moving a patient along a movement path as well as in a rotated and elevated position. FIGS. 10(*a*) and 10(*b*) are side views of the embodiment of FIGS. 10(*a*) and 10(*b*) for positioning a patient along a vertical axis.

Naturally for the medical equipment there is a standard control unit (not illustrated) to control the operation and, in particular, to control the operation of the positioning system.

By means of the invention it is possible to realise a structure which is connected mechanically to the medical equipment (in particular to the magnet of a Magnetic Resonance Imaging device), which is capable of positioning, at the centre of the magnetic area, any part whatsoever of the anatomy of a patient positioned on the bench fitted with reclinable and non-reclinable parts. All of this without introducing ferromagnetic parts or electrically conductive parts inside the magnetic which are critical for the quality of the images.

It is intended that the characteristics which have been described above with reference to just a few different arrangements can be combined, provided that these are compatible, with the characteristics of other arrangements described or other different configurations that can be understood by a technical expert, provided that the same do not go outside the boundaries of the present Invention.

The invention claimed is:

1. A magnetic resonant imaging system comprising:
 a main magnet having opposing poles, positioned along a horizontal axis, that define an open magnetic resonance imaging area configured to detect a magnetic field generated by the main magnet; and
 a transport system comprising:
  a bench comprising
   at least two parts configured to support a patient, that is capable of moving the patient into and out of the open magnetic resonance imaging area with the at least two parts of the bench being capable of forming and maintaining the form of a chair shaped seat, while the patient is being moved into and out of the open magnetic resonance imaging area of the main magnet,
   wherein said at least two parts are pivotally attached to one another at, at least one rotation point around the horizontal axis, and
  a support structure configured to support the bench, wherein the support structure comprises:
   a track passing between said opposing poles of the main magnet, that is also at a fixed position relative to the main magnet, such that the bench moves along a movement path on the fixed position of the track into and out of the open magnetic resonance imaging area, and
   wherein at least one part, of the at least two parts of the bench which are configured to support a patient is rotatable at said at least one rotation point while within the open magnetic resonance imaging area in order to position the patient in any desired slanted position after the patient is, or has been moved by the bench and positioned within the open magnetic resonance imaging area which allows any part of the anatomy of the patient, on the bench, to be properly positioned at the center of the open magnetic resonance imaging area.

2. The magnetic resonant imaging system of claim 1, wherein the bench comprises:
a non-reclinable support part and
at least one reclinable support part rotatably coupled to the non-reclinable support part at the at least one rotation point.

3. The magnetic resonant imaging system of claim 2, wherein two reclinable support parts are rotatably coupled to the opposing ends of the non-reclinable support part at corresponding rotation points.

4. The magnetic resonant imaging system of claim 1, wherein said track comprises a transmission belt loop that is made from a non-metallic material and is configured to move the bench along the movement path.

5. The magnetic resonant imaging system of claim 4, further comprising at least one pulley to engage with the transmission belt loop at a drive point.

6. The magnetic resonant imaging system of claim 1, wherein said transport system comprises a pantograph mechanism, wherein a rotational movement at a first part of the bench corresponds to a rotational movement at a second part of the bench.

7. The magnetic resonant imaging system of claim 6, wherein said pantograph mechanism comprises a plurality of substantially parallel telescopic supports correspondingly coupled to the first part and to the second part of the bench.

8. The magnetic resonant imaging system of claim 1, wherein the bench is rotated to a desired position in response to a control signal.

9. The magnetic resonant imaging system of claim 1, wherein said transport system comprises movable parts configured to adjust the position of the bench, said movable parts comprising a non-ferromagnetic material.

10. The magnetic resonant imaging system of claim 1, wherein the magnet has a substantially U-shape.

11. The magnetic resonant imaging system of claim 1, further comprising a ratchet mechanism configured to position the bench in a substantially rotated position.

12. The magnetic resonant imaging system of claim 1, wherein the transport system is movable along a vertical axis in order to elevate and lower the bench.

13. The magnetic resonant imaging system of claim 1, wherein the at least one part of the bench is rotatable within the open magnetic resonance imaging area and around an axis parallel to the horizontal axis in order to position the patient in a desired slanted position.

14. The magnetic resonant imaging system of claim 1, wherein the at least one part of the bench is further rotatable around a vertical axis in order to position the patient in a desired position.

15. The magnetic resonant imaging system of claim 1, wherein the at least one part of the bench is further rotatable in order to position the patient in a desired slanted position before the patient is moved within the open magnetic resonance imaging area.

* * * * *